United States Patent [19]

Langston et al.

[11] Patent Number: 4,928,681

[45] Date of Patent: May 29, 1990

[54] WOUND DRESSING

[75] Inventors: Richard D. Langston, Wokingham; Frances C. Webb, Maidenhead; Simon C. McBeath, Poole, all of United Kingdom

[73] Assignee: Charcoal Cloth Limited, Berkshire, England

[21] Appl. No.: 213,663

[22] Filed: Jun. 30, 1988

[30] Foreign Application Priority Data

Jul. 1, 1987 [GB] United Kingdom ................. 8715421

[51] Int. Cl.⁵ ............................................. A61L 15/00
[52] U.S. Cl. ..................................... 128/156; 128/155
[58] Field of Search ................................ 128/155, 156

[56] References Cited

U.S. PATENT DOCUMENTS

| 4,341,217 | 7/1982 | Ferguson et al. | 604/375 X |
| 4,726,978 | 2/1988 | Simpson | 428/198 |
| 4,817,594 | 4/1989 | Juhasz | 128/155 |

Primary Examiner—Randall L. Green
Assistant Examiner—N. Paul
Attorney, Agent, or Firm—Jeffers, Hoffman & Niewyk

[57] ABSTRACT

A wound dressing which comprises, in order:
a layer of a permeable material suitable for putting in contact with the wound;
a layer of a charcoal fabric;
an absorbent pad; and
one or more layers which protect and substantially prevent liquid strike-through.

16 Claims, 1 Drawing Sheet

WOUND DRESSING

This invention relates to wound dressings, and particularly to dressings intended for application to wounds in contaminated environments.

BACKGROUND OF THE INVENTION

The utility of carbonised fabric in surgical dressings has been appreciated for over 50 years. EP-A-0386867 discloses surgical dressings comprising woven or entangled carbonised fibres, e.g. as supports for therapeutic or antiseptic materials.

Surgical dressings using activated charcoal impregnated with anti-bacterial agent, within an envelope of permeable material, are disclosed in EP-A-0053936. The incorporated agent inherently limits the bacteria-absorbing characteristics of the charcoal.

EP-A-0099758 discloses a 3-layer composite (but not integral) wound dressing comprising a semi-permeable membrane, a permeable supporting and reinforcing layer, and a non-stick, self-sealing biodegradable tissue interface. The permeable layer may be an activated carbon cloth.

WO-A-8605970 and WO-A-8605871 disclose integral anti-bacterial wound dressings comprising a layer of charcoal fabric such as activated charcoal cloth enveloped within layers of permeable material. The layers of permeable material surround the charcoal fabric and are bound together in the surrounding area.

The standard requirements of a field dressing are high fluid absorbency, high mechanical protection, and the application of even compression to the wound site. The anti-bacterial advantages of charcoal cloth have been combined with the standard requirements in a known field dressing which comprises a wound-facing layer, a layer of charcoal cloth, an absorbent pad, a layer which substantially prevents liquid strike-through, and an outer layer of a cover material to which bandages are attached. The dressing can therefore be secured in close contact with a wound, to compress it, absorb blood and adsorb bacteria, thus reducing the risk of infection.

Further protection may be desirable in an environment in which biological or chemical contaminants may be present. It is nevertheless impossible or impractical to make a perfect seal against penetration of harmful contaminants to a wound, especially around the knee or another joint.

SUMMARY OF THE INVENTION

A wound dressing according to the present invention comprises, in order, a layer of a permeable material suitable for putting in contact with the wound, a first layer of a charcoal fabric, an absorbent pad, (preferably) a layer which substantially prevents liquid (and often also fluid) strike-through, and an outer material which substantially prevents direct contamination of a wound.

The essential difference between the novel dressing and the known field dressing including charcoal cloth, is the presence of the outer, protective layer. This outer layer serves to protect against any direct contamination in the atmosphere with which it may come into contact; if there are contaminant substances which bypass the cover and which would otherwise enter the wound via the often inevitably incomplete seal between the dressing and the wearer, it will be absorbed by the first layer of charcoal fabric.

DESCRIPTION OF THE INVENTION

Figure 1:
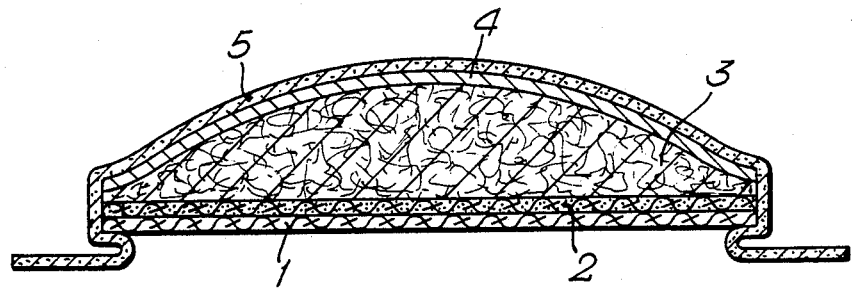
FIGS. 1 and 2 are highly schematic cross-sections of two embodiments of the invention and are shown by way of example only.

FIG. 1 of the drawings shows a layer 1 of a permeable material, a layer 2 of charcoal cloth, a pad 3 of an adsorbent material such as cotton, a layer 4 of a material designed to prevent fluid strike-through, and an outer layer 5 of a composite material including an activated charcoal material. The drawing shows a preferred embodiment of the invention, in the sense that the layer 5 overlaps the layers/pad 1, 2, 3 and 4. The overlapping area of layer 5 minimises the risk of any contamination of the wound in two ways; firstly by providing a greater protective area than the size of the dressing pad, and secondly by providing an adsorptive surface between the edge of the outer cover and the edge of the open wound. As an alternative, the overlapping area of layer 5 could be composed of an impermeable material, e.g. butyl rubber. However, although this will also minimise the risk of contamination of the wound, by providing a greater protective area than the size of the dressing pad, it will not provide an adsorptive surface between the edge of the outer cover and the edge of the wound. The overlap may be, for example, 10 to 150 mm in at least one direction, and perhaps in two or all four directions around an essentially rectangular wound dressing.

Figure 2:
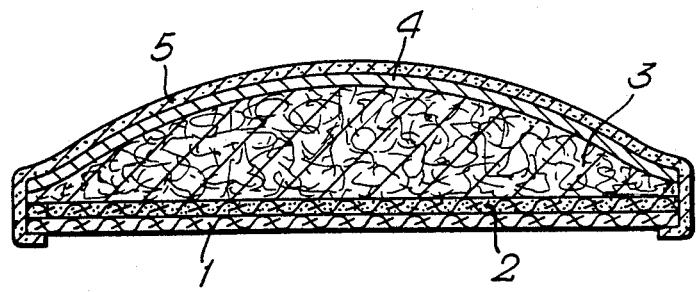

FIG. 2 of the drawings shows the same layers/pad 1, 2, 3, 4, 5 as FIG. 1, but the layer 5 does not overlap the layers/pad 1, 2, 3 and 4. Again, as an alternative, the layer 5 could be composed of an impermeable material, for example butyl rubber. However, although this will provide protection against direct contamination with which it comes into contact, it may allow liquid contamination to migrate around the edge of the dressing. In this alternative, layer 4 would no longer be necessary.

In general, therefore, the outer layer may be an impermeable material such as butyl rubber or it may be of a composite material which includes a second charcoal fabric, preferably activated charcoal cloth. The composite material is, for example, as described in our International PCT patent application designating the U.S. filed on June 1988, each claiming priority from our British Patent Application No. 8714535, filed June 1987, and entitled "CBW Protective Material"; the content of said PCT application is incorporated herein by way of reference.

Unless the outer layer is an impermeable material, it will usually comprise a composite material of which the outer layer may be woven or non-woven, and will usually have a degree of oil-repellency. An example of a suitable material is a two-by-one twill fabric having a polyamide warp thread and a modified acrylic weft thread, e.g. at a make-up weight of 118 g/m$^2$. Other examples are woven or non-woven aramid fibre materials, e.g. as sold as Nomex (Trade Mark), another fire-resistant or chemical-resistant breathable fabric, or a water-resistant breathable fabric such as Gore-tex (Trade Mark).

This outer material should preferably also be treated with a, say, silicone water-repellent and a fire-retardant additive. The material will usually be showerproof but is not necessarily waterproof.

Any form of charcoal cloth or felt may be used in the invention, but activated charcoal cloth (ACC) is preferred. ACC is an activated carbon adsorbent available in a woven or non-woven form.

A dressing of the invention may be constructed in situ. In other words, the wound-facing layer, absorbent pad, charcoal fabric and any cover material may be applied to a wound to give the desired sequence individually or in combinations of two or more. For example, the wound-facing layer and the absorbent pad may be applied underneath a protective material comprising a composite material as described above.

A product of the invention may be provided with ties or other means for securing it in contact with a wound, in conventional manner.

A wound dressing of the invention is very suitable for use in tropical conditions, where open wounds are at risk from serious infection within a short period of time, and in hostile environments where wounds may be unattended for some time; the novel wound dressing provides all the standard features of a field dressing together with the property of reducing the risk of infection and providing protection against chemical and biological contamination.

What is claimed is:

1. A wound dressing which comprises, in order:
   a layer of a permeable material suitable for putting in contact with the wound;
   a layer of a charcoal fabric;
   an absorbent pad; and
   one or more layers including an impermeable material which protect and substantially prevent liquid strike-through.

2. A wound dressing according to claim 1, wherein said one or more layers comprise a protective layer including a charcoal fabric.

3. A wound dressing according to claim 1, wherein said absorbent pad comprises cotton.

4. A wound dressing according to claim 1, wherein said one or more layers include a protective layer overlapping the other layers and said pad.

5. A wound dressing according to claim 4, wherein said protective layer overlaps the other layers and said pad by 10 to 150 mm in at least one of the length and width direction.

6. A wound dressing according to claim 1, wherein said charcoal fabric is activated charcoal cloth.

7. A wound dressing according to claim 2, wherein each said charcoal fabric is activated charcoal cloth.

8. A wound dressing according to claim 1, which comprises tapes or other means for securing the dressing in close contact with the wound.

9. A wound dressing which comprises, in order:
   a layer of a permeable material suitable for putting in contact with the wound;
   a layer of a charcoal fabric;
   an absorbent pad; and
   one or more layers comprising a protective layer including a charcoal fabric, which protect and substantially prevent liquid strike-through.

10. A wound dressing according to claim 9, wherein said one or more layers comprise an impermeable material.

11. A wound dressing according to claim 9, wherein said absorbent pad comprises cotton.

12. A wound dressing according to claim 9, wherein said one or more layers include a protective layer overlapping the other layers and said pad.

13. A wound dressing according to claim 12, wherein said protective layer overlaps the other layers and said pad by 10 to 150 mm in at least one of the length and width direction.

14. A wound dressing according to claim 9, wherein said charcoal fabric in said protective layer is activated charcoal cloth.

15. A wound dressing according to claim 9, wherein each said charcoal fabric is activated charcoal cloth.

16. A wound dressing according to claim 9, which comprises tapes or other means for securing the dressing in close contact with the wound.

* * * * *